United States Patent [19]

Pebler et al.

[11] 4,214,967
[45] Jul. 29, 1980

[54] TECHNIQUE FOR REDUCING SOLID ELECTROLYTE CELL DRIFT

[75] Inventors: Alfred R. Pebler, Penn Hills; Roswell J. Ruka, Churchill Borough, both of Pa.

[73] Assignee: Westinghouse Electric Corp., Pittsburgh, Pa.

[21] Appl. No.: 849,590

[22] Filed: Nov. 8, 1977

[51] Int. Cl.² .................................................. G01N 27/58
[52] U.S. Cl. .......................................................... 204/195 S
[58] Field of Search .................................... 204/1 S, 195 S

[56] References Cited

U.S. PATENT DOCUMENTS

| | | | |
|---|---|---|---|
| 3,791,954 | 2/1974 | Noda et al. | 204/1 S |
| 3,864,231 | 2/1975 | Richardson | 204/195 S |
| 3,909,385 | 9/1975 | Spielberg et al. | 204/195 S |
| 3,915,830 | 10/1975 | Isenberg | 204/195 S |
| 3,928,161 | 12/1975 | McIntyre et al. | 204/195 S |
| 4,040,929 | 8/1977 | Bauer | 204/195 S |

*Primary Examiner*—G. L. Kaplan
*Attorney, Agent, or Firm*—M. P. Lynch

[57] ABSTRACT

In a gas analyzer employing a disc-shaped oxygen ion conductive solid electrolyte cell, having electrodes disposed on opposite surfaces thereof, and secured at its edge within a tubular member by noble metal braze, a non-conducting ceramic layer is disposed between the solid electrolyte material and the braze to minimize cell drift which could otherwise occur if the braze interacted as a cell "electrode".

3 Claims, 3 Drawing Figures

U.S. Patent
Jul. 29, 1980
4,214,967
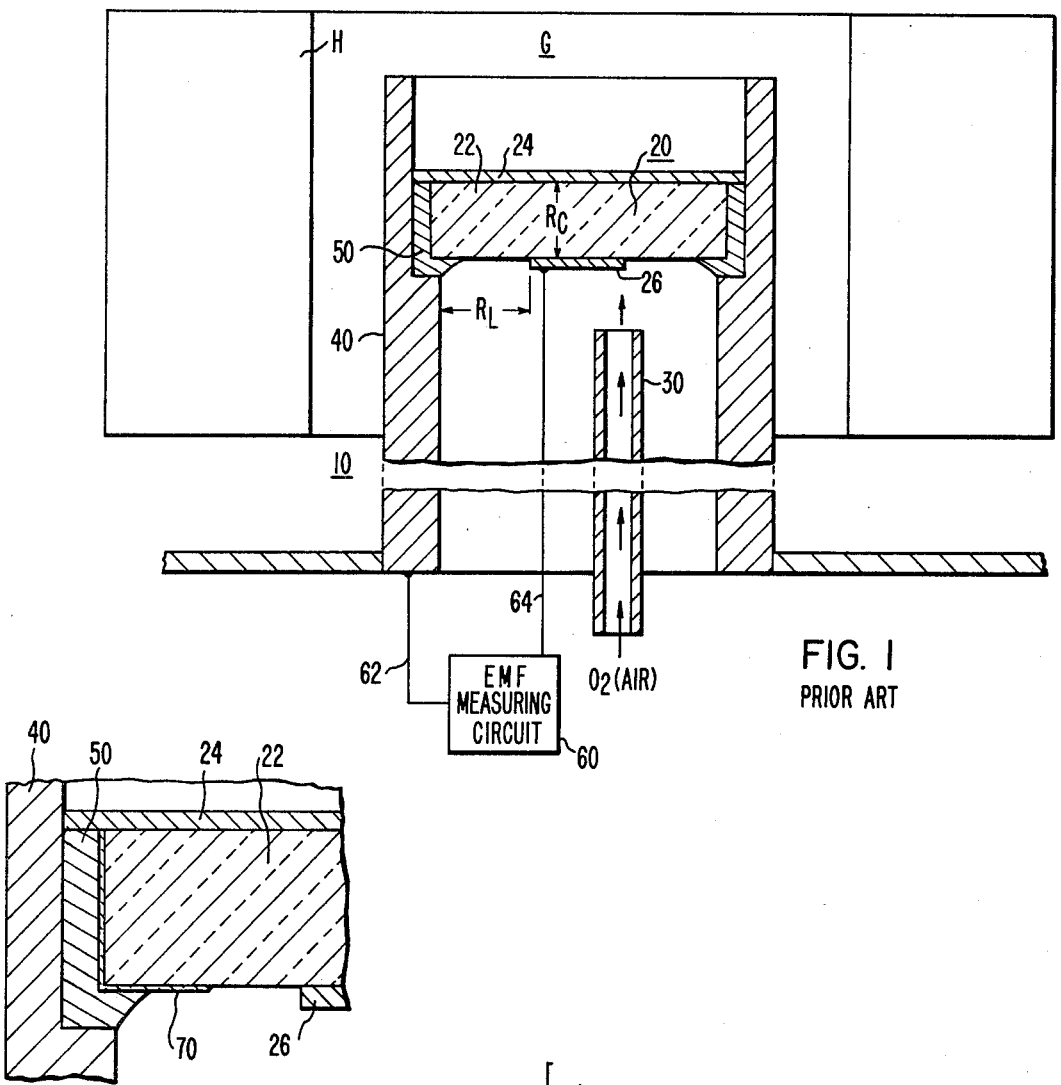
FIG. 1
PRIOR ART
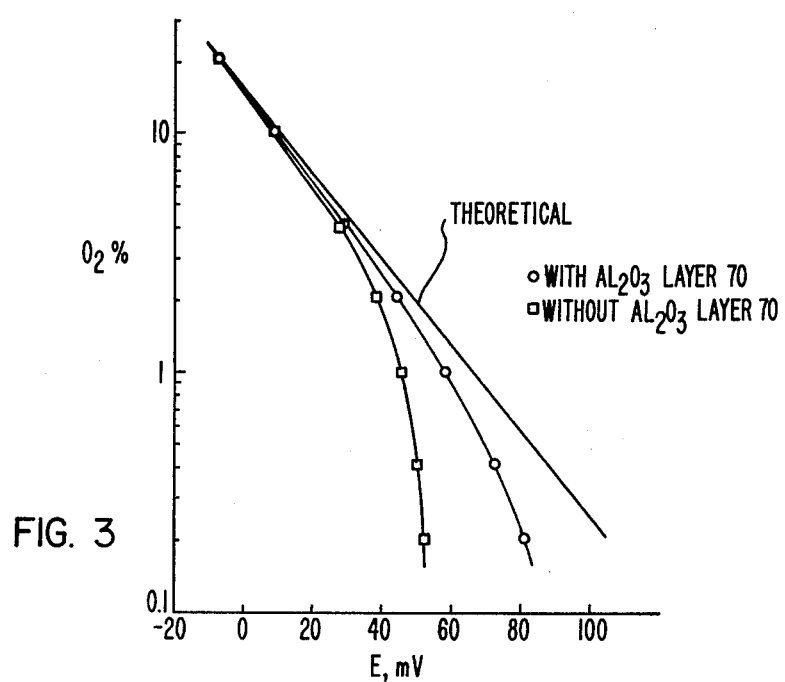
FIG. 2
FIG. 3

TECHNIQUE FOR REDUCING SOLID ELECTROLYTE CELL DRIFT

BACKGROUND OF THE INVENTION

In commercially available gas measuring probes, such as that described in U.S. Pat. No. 3,928,161, assigned to the assignee of the present invention and incorporated herein by reference, which employ a solid electrolyte electrochemical cell having electrodes disposed on opposite surfaces thereof, the electrodes, which are typically platinum, undergo a physical deterioration when exposed to reducing industrial atmospheres containing sulfur compounds and highly corrosive flue gases. The disintegration or deterioration of the electrode results in a loss of contact with the solid electrolyte substrate which in turn results in an increase in cell resistance.

In oxygen analyzer probes such as that described in the above-identified U.S. Patent, wherein the solid electrolyte electrochemical cell is in the form of a disc which is secured within a tubular member by a noble metal braze, the braze exhibits the same characteristics as the cell electrode and assumes the function of an additional oxygen electrode when the electronic conductivity across a cell electrode diminishes due to cell electrode deterioration. This condition results in an electrolytic leakage current through the electrolyte near the braze which changes the EMF produced by the electrochemical cell.

SUMMARY OF THE INVENTION

There is disclosed herein with reference to the accompanying drawings a technique for minimizing the undesirable "electrode" action of the noble metal braze by disposing a nonconducting ceramic layer between the solid electrolyte member of the solid electrolyte electrochemical cell and the braze.

DESCRIPTION OF THE DRAWINGS

The invention will become more readily apparent from the following exemplary description in connection with the accompanying drawings:

FIG. 1 is a Prior Art sectioned schematic illustration of a gas analyzer probe;

FIG. 2 is a partial sectioned illustration of the gas analyzer probe of FIG. 1 incorporating the invention;

FIG. 3 is a graphical illustration of the operation of the gas analyzer probe of FIG. 1 with and without the inventive contribution.

DESCRIPTION OF THE PREFERRED EMBODIMENT

Referring to FIG. 1, there is a sectioned schematic illustration of a Prior Art gas-probe assembly 10, similar to that described in the above-referenced United States patent, wherein the gas-probe assembly 10 is inserted in a monitored gas environment G and maintained at a stable operating temperature by the heater H. The gas-probe assembly 10 includes a solid electrolyte cell 20 which consists of a solid electrolyte member 22 and electrodes 24 and 26 disposed on opposite surfaces thereof. In the application of the gas-probe assembly 10 for monitoring the oxygen content of the monitored gas environment G, the solid electrolyte member 22 consists of an oxygen ion conductive solid electrolyte material. The composition and operation of an oxygen ion conductive solid electrolyte cell is described in detail in the above-referenced United States patent as well as in Reissue patent U.S. Pat. No. 28,792, which is assigned to the assignee of the present invention and incorporated herein by reference. The electrodes 24 and 26 are typically a noble metal such as platinum. Electrode 24 is exposed to the monitored gas environment G and functions as a sensing electrode while electrode 26 is exposed to a stable reference oxygen environment and functions as an oxygen reference electrode. The reference oxygen environment is typically illustrated as being provided by the flow of air through an air inlet tube 30.

The solid electrolyte electrochemical cell 20 is secured within a tubular probe member 40 by a noble metal braze 50, such as a gold/platinum braze, securing the edge of the solid electrolyte electrochemical cell 20 to the tubular member 40. A noble metal braze is selected because it will withstand the gas environment G without oxidizing and deteriorating. However, due to the fact the noble metal braze 50 exhibits the same characteristics as the noble metal electrodes 24 and 26, the braze 50 can, under the conditions described, assume the function of an "electrode". Prior to the brazing operation, the edge of the solid electrolyte is often metallized with a coating of platinum to facilitate bonding between the braze 50 and the solid electrolyte 22.

In the embodiment illustrated in FIG. 1, the sensing electrode 24 extends across the surface of the solid electrolyte member 22 and is in electrical contact with the metal tubular member 40 which functions as an electrical conductor. An EMF measuring circuit 60 is electrically connected to the sensing electrode 24 by an electrical lead 62 which is connected to the tubular member 40, and to reference electrode 26 by electrical lead 64. The solid electrolyte electrochemical cell 20 generates an EMF across the electrodes 24 and 26 which is measured by the EMF measuring circuit 60 as an indication of the oxygen partial pressure of the monitored gas environment G.

This EMF is generated in accordance with the Nernst equation:

$$E_o = (RT/4F)\ln(P_{O_2}'/P_{O_2}'') = C\ln(P_{O_2}'/P_{O_2}'')$$

where C is a constant, $P_{O_1}$ is the partial pressure at the reference electrode 26, $P_{O_2}$ is the oxygen partial pressure of the monitored gas environment G at the sensing electrode 24, and $E_o$ is the theoretical cell voltage developed in response to differential oxygen partial pressure across the solid electrolyte 22.

Initially, electrodes 24 and 26 represent integral coatings of a suitable electrode material. In the embodiment of FIG. 1, the cell resistance $R_c$ is very small compared to the potential leakage resistance $R_L$ defined between the braze 50 and the reference electrode 26. However, as the sensing electrode 24 is exposed to highly corrosive industrial environments, the sensing electrode 24 begins to disintegrate, thus reducing the contact surface between the sensing electrode 24 and the solid electrolyte member 22, thereby causing an increase in the cell resistance $R_c$. As the cell resistance $R_c$ increases and approaches the leakage resistance $R_L$, the measured cell output voltage drops for a given oxygen partial pressure difference. The measured cell output voltage can be expressed as follows:

$$E = E_o(R_L/R_L + R_c)$$

Moreover, as the cell resistance $R_c$ increases, it may become dependent on cell voltage (non-ohmic characteristics). The combined effect on the response of the electrochemical cell 20 is manifested as a cell drift.

It has been determined experimentally that the addition of a thin, i.e., 1–2 μm, nonconducting layer 70, as shown in FIG. 2, between the braze 50 and the solid electrolyte material 22, substantially reduces the cell drift in the presence of deterioration of the sensing electrode 24.

The thin layer 70 is a nonconductive ceramic layer which prevents the transfer of oxygen from the surface of the braze 50 to the solid electrolyte member 22. The layer 70 can typically consist of a thin layer of alumina ($Al_2O_3$) which may be applied by RF sputtering. The essential characteristics for the nonconductive ceramic layer include:

(a) negligible ionic and electronic conductivity relative to that of the solid electrolyte;
(b) thermal expansion similar to solid electrolyte; and
(c) chemically inert relative to the braze and the solid electrolyte.

Thus, suitable materials other than alumina include $Si_3N_4$, BeO, $SiO_2$, etc.

An evaluation of a probe assembly similar to that illustrated in FIG. 1 with and without the addition of the nonconducting ceramic layer 70 between the braze 50 and the solid electrolyte member 22 is graphically illustrated in FIG. 3. The slight departure of the curve representing the probe assembly including the layer from the theoretical straight line indicates that an increase in the thickness of the layer 70 would provide a desired increase in the electrical separation between the braze 50 and the solid electrolyte member 22.

What is claimed is:

1. A method of securing a disc-shaped oxygen ion conductive solid electrolyte electrochemical cell within a tubular metal support member to minimize cell drift as a result of cell electrode deterioration, comprising the steps of:

disposing an oxygen transfer barrier in contact with the edge of said disc-shaped oxygen ion conductive solid electrolyte electrochemical cell, said barrier being a thin ceramic layer exhibiting negligible oxygen ion conductivity;

brazing said cell with a noble metal braze within said metal tubular support member, said oxygen transfer barrier substantially preventing the transfer of oxygen between said noble metal braze and said solid electrolyte electrochemical cell to prevent said noble metal braze from functioning as a cell electrode, said thin ceramic layer being of a material exhibiting a thermal expansion coefficient similar to that of the solid electrolyte electrochemical cell and being chemically inert with respect to said noble metal braze and said solid electrolyte electrochemical cell.

2. The method of claim 1 wherein said thin layer of ceramic material is of a thickness of between approximately 1–2 μm.

3. In a method as claimed in claim 1 wherein said ceramic material is selected from the group consisting of $Al_2O_3$, $Si_3N_4$, BeO and $SiO_2$.

* * * * *